US012778451B2

(12) United States Patent
Shankar et al.

(10) Patent No.: US 12,778,451 B2
(45) Date of Patent: Nov. 3, 2026

(54) ELECTRONIC RING FOR OPTIMIZING HEALTH AND FITNESS PARAMETERS MEASURED BY OPTICAL SENSORS

(71) Applicant: ULTRAHUMAN HEALTHCARE PVT LTD, Karnataka (IN)

(72) Inventors: Apoorv Shankar, Bangalore (IN); Yogansh Namdeo, Karnataka (IN); Anoop Jayan, Bangalore (IN); Adhit Shet, Bangalore (IN); Vatsal Singhal, Bangalore (IN)

(73) Assignee: ULTRAHUMAN HEALTHCARE PVT LTD, Karnataka (IN)

( * ) Notice: Subject to any disclaimer, the term of this patent is extended or adjusted under 35 U.S.C. 154(b) by 0 days.

(21) Appl. No.: 19/038,017

(22) Filed: Jan. 27, 2025

(65) Prior Publication Data

US 2025/0204807 A1 Jun. 26, 2025

Related U.S. Application Data

(63) Continuation of application No. 18/850,956, filed as application No. PCT/IN2023/050290 on Mar. 27, 2023, now abandoned.

(30) Foreign Application Priority Data

Mar. 31, 2022 (IN) ............................ 202241019496

(51) Int. Cl.
*A61B 5/00* (2006.01)
*A61B 5/024* (2006.01)
(Continued)

(52) U.S. Cl.
CPC ........ *A61B 5/1032* (2013.01); *A61B 5/02416* (2013.01); *A61B 5/0537* (2013.01);
(Continued)

(58) Field of Classification Search
CPC . A61B 5/1032; A61B 5/02416; A61B 5/6826; A61B 5/7264; A61B 5/7246
See application file for complete search history.

(56) References Cited

U.S. PATENT DOCUMENTS

2008/0265170 A1* 10/2008 Ales ...................... G01J 1/0219 340/600
2009/0245603 A1* 10/2009 Koruga .................. A61B 5/444 382/128
(Continued)

FOREIGN PATENT DOCUMENTS

CN 109363652 B 5/2021
TW M610327 U 4/2021
(Continued)

OTHER PUBLICATIONS

International Search Report and Written Opinion for International Application No. PCT/IN2023/050290, dated May 30, 2024. (7 Pages).
(Continued)

*Primary Examiner* — James Moss
(74) *Attorney, Agent, or Firm* — Renner, Otto, Boisselle & Sklar, LLP

(57) ABSTRACT

The proposed invention relates to a method of determining health and fitness parameters of a user. The method comprises obtaining, by a colour sensor (304), intensity values of reflections of light transmitted by the colour sensor on a skin of a user. The intensity values are classified into a plurality of skin types to determine a skin tone of the user. The plurality of skin types are associated with correction factors. The method further comprises obtaining, by a Photoplethysmography (PPG) sensor (302), PPG values associated with health and fitness parameters of the user. The correction factors may be multiplied by the PPG values to optimize the
(Continued)

health and fitness parameters based on the skin tone of the user.

6 Claims, 5 Drawing Sheets

(51) Int. Cl.

| | |
|---|---|
| ***A61B 5/0537*** | (2021.01) |
| ***A61B 5/103*** | (2006.01) |
| ***A61B 5/1455*** | (2006.01) |

(52) U.S. Cl.
CPC ........ *A61B 5/14551* (2013.01); *A61B 5/6826* (2013.01); *A61B 5/7264* (2013.01)

(56) References Cited

U.S. PATENT DOCUMENTS

| | | | | |
|---|---|---|---|---|
| 2015/0057552 | A1* | 2/2015 | Mohamad Hani | A61B 5/443 600/477 |
| 2017/0303861 | A1* | 10/2017 | Bechtel | A61B 5/14552 |
| 2021/0330209 | A1* | 10/2021 | Nadeau | A61B 5/6824 |
| 2023/0181112 | A1* | 6/2023 | Voigt | A61B 5/0022 600/301 |

FOREIGN PATENT DOCUMENTS

| | | | | |
|---|---|---|---|---|
| WO | WO-2014137918 | A1 * | 9/2014 | A61B 5/681 |
| WO | 2021245203 | A1 | 12/2021 | |

OTHER PUBLICATIONS

International Preliminary Report on Patentability received for PCT Patent Application No. PCT/IN2023/050290 , mailed on Oct. 10, 2024, 7 pages.

* cited by examiner

ELECTRONIC RING FOR OPTIMIZING HEALTH AND FITNESS PARAMETERS MEASURED BY OPTICAL SENSORS

CROSS-REFERENCE TO RELATED APPLICATIONS

This application is a continuation of U.S. application Ser. No. 18/850,956, filed Sep. 25, 2024, which is a 371 application of PCT/IN2023/050290, filed Mar. 27, 2023, which claims priority to India patent application No. 202241019496, filed Mar. 31, 2022, which applications are incorporated herein by reference.

FIELD OF INVENTION

The present invention relates to optimization of health and fitness parameters measured by a wearable device, and specifically relates to optimization of health and fitness parameters based on skin tone of users.

BACKGROUND

Regular health and fitness monitoring is important for accomplishing long term health and wellness goals. Traditionally, fitness monitoring required manual recording of one's physical exercise activities. However, such manual recording is inconvenient and often inaccurate.

Generally, detection of one's health parameters requires stationary medical equipments such as an ECG machine, BP monitoring machine etc, which are bulky and inconvenient to use. Consequently, a person always on the move is unable to keep a track of his physical health parameters to maintain his health in a good condition, thereby disabling him to have more control on his daily lifestyle, physical activities and habits. Needless to say, lack of knowledge about one's own body and inability to make conscious data driven lifestyle changes impacts one's health and fitness in the long run.

With advancement in technology, portable machines for detection of body parameters have been developed. Such machines may utilize sensors for measurement of health and fitness parameters.

Sensors used for detection of health and fitness parameters may not always produce accurate results, especially optical sensors that rely on detection of light reflected from the skin of a user. As the melanin present in skin of the users absorb a portion of the light emitted by a light element, skin tone of a user has an adverse effect on accuracy of detection of health and fitness parameters. Detection of health and fitness parameters is further inhibited by factors such as tattoos and hair on the skin of a user. Thus, there remains a need of a wearable device that measures health and fitness parameters of users having different skin tones with accuracy and precision.

OBJECTS OF THE INVENTION

A general objective of the present invention is to offer an efficient system of optimization of measured health and fitness parameters.

Another objective of the invention is to provide a cost-effective system for measurement of health and fitness parameters.

Yet another objective of the invention is to provide a universal system for measurement of health and fitness parameters across users of all skin tones.

Still another objective of the invention is to optimize readings of health and fitness parameters measured using optical sensors.

SUMMARY OF THE INVENTION

The summary is provided to introduce aspects related to an electronic ring for optimizing health and fitness parameters measured by optical sensors. The electronic ring may be worn over a finger. The electronic ring may include different sensors for monitoring the health and fitness parameters of users.

The proposed invention relates to a method of determining health and fitness parameters of a user. The method comprises obtaining, by a colour sensor, intensity values of reflections of light transmitted by the colour sensor on a skin of a user. The intensity values are classified into a plurality of skin types to determine a skin tone of the user. The plurality of skin types are associated with correction factors. The method further comprises obtaining, by a Photoplethysmography (PPG) sensor, PPG values associated with health and fitness parameters of the user. The correction factors may be multiplied by the PPG values to optimize the health and fitness parameters based on the skin tone of the user.

In one aspect, the PPG sensor identifies a preliminary skin tone of the user.

In one aspect, when the preliminary skin tone identified by the PPG sensor is different from the skin tone identified by the colour sensor, readings of the PPG sensor are filtered by a probabilistic model to determine a final skin tone.

In one aspect, the method further comprises determining confidence of the readings of the PPG sensor based on a value of an auto-correlation function associated with the readings of the PPG sensor. The value of auto-correlation function ranges from −1 to +1.

In one aspect, the value of the auto-correlation function depends on a level of body hydration of the user.

In one aspect, the plurality of skin types include six skin types according to Fitzpatrick skin type scale.

In one aspect, the health and fitness parameters include one or more of heart-rate, Heart Rate Variability (HRV), a hydration level, and blood oxygen saturation (SPO2) level.

The present invention further relates to an electronic ring for monitoring fitness and health parameters of a user. The electronic ring comprises a colour sensor for obtaining intensity values of reflections of light transmitted by the colour sensor on a skin of a user. The electronic ring further comprises a PPG sensor for obtaining PPG values associated with health and fitness parameters of the user. The electronic ring further comprises a microcontroller for classifying the intensity values into a plurality of skin types to determine a skin tone of the user, wherein the plurality of skin types are associated with correction factors and multiplying the correction factors and the PPG values to optimize the health and fitness parameters based on the skin tone of the user.

In one aspect, the PPG sensor further identifies a preliminary skin tone of the user. When the preliminary skin tone identified by the PPG sensor is different from the skin tone identified by the colour sensor, readings of the PPG sensor are filtered by a probabilistic model to determine a final skin tone.

Other aspects and advantages of the invention will become apparent from the following description, taken in conjunction with the accompanying drawings, illustrating by way of example the principles of the invention.

BRIEF DESCRIPTION OF THE DRAWINGS

The accompanying drawings constitute a part of the description and are used to provide further understanding of the present invention. Such accompanying drawings illustrate the embodiments of the present invention which are used to describe the principles of the present invention. The embodiments are illustrated by way of example and not by way of limitation in the figures of the accompanying drawings in which like references indicate similar elements. It should be noted that references to "an" or "one" embodiment in this invention are not necessarily to the same embodiment, and they mean at least one. In the drawings.

DETAILED DESCRIPTION OF THE INVENTION

The detailed description set forth below in connection with the appended drawings is intended as a description of various embodiments of the present invention and is not intended to represent the only embodiments in which the present invention may be practiced. Each embodiment described in this disclosure is provided merely as an example or illustration of the present invention, and should not necessarily be construed as preferred or advantageous over other embodiments. The detailed description includes specific details for the purpose of providing a thorough understanding of the present invention. However, it will be apparent to those skilled in the art that the present invention may be practiced without these specific details.

Figure 1:
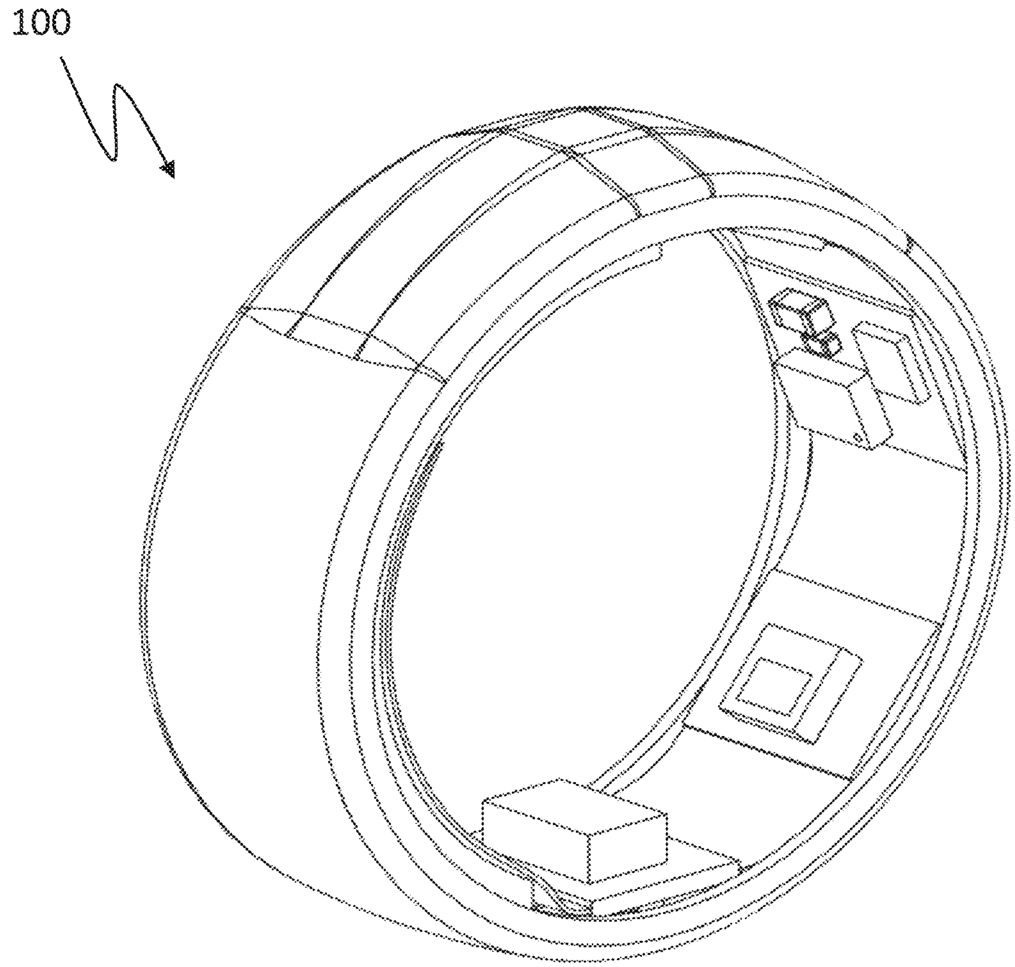
FIG. 1 illustrates a front perspective view of an electronic ring, in accordance with an embodiment of the present invention.

The proposed invention relates an electronic ring for optimizing health and fitness parameters of users. The electronic ring may be worn over a finger. FIG. 1 illustrates a front perspective view of an electronic ring (100), in accordance with an embodiment of the present invention. The electronic ring (100) may be developed in different sizes to fit over different fingers of different users. The electronic ring (100) may include different sensors for monitoring the health and fitness parameters of users. Types, placement, and working of the sensors used in the electronic ring (100) is described henceforth.

Figure 2:
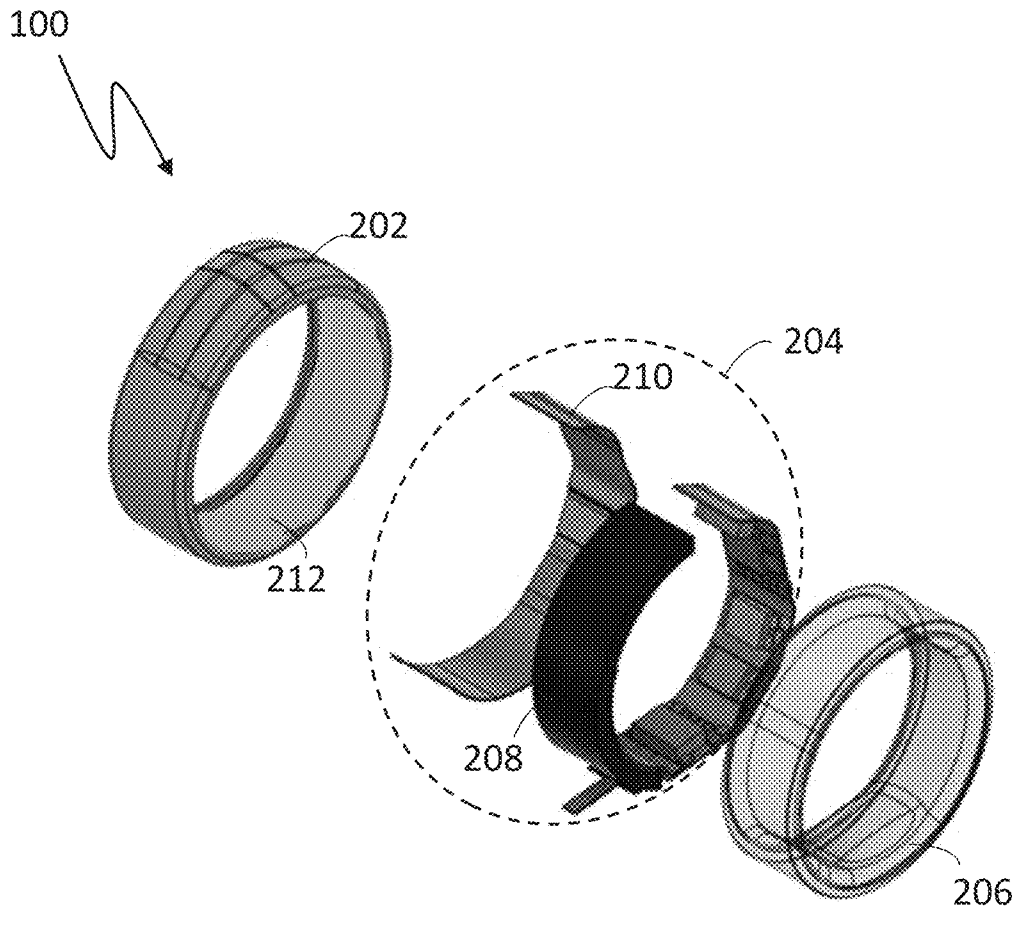
FIG. 2 illustrates an exploded view of an electronic ring having a multi-layered arrangement, in accordance with an embodiment of the present invention.

FIG. 2 illustrates an exploded view of the electronic ring (100) having multi-layered arrangement, in accordance with an embodiment of the present invention. The electronic ring (100) may comprise an outer layer (202), a middle layer (204), and an inner layer (206). The outer layer (202) may be made of a rigid, antirust or thermally conductive material, or a material having all such properties. The middle layer (204) may be positioned between the outer layer (202) and the inner layer (206). The middle layer (204) may include a Printed Circuit Board (PCB) (208) and a battery (210). The PCB (208) may be flexible, semi-flexible, or rigid. The PCB (208) may house one or more sensors to capture a plurality of health and fitness parameters of a user.

The inner layer (206) of the electronic ring (100) positioned below the PCB (208) may come in contact of the user's finger once the user wears the electronic ring (100). The inner layer (206) may be made of a semi-transparent, translucent, or completely transparent, water-resistant material, such as glass, plastic, resin, or silicone. The inner layer (206) may be transparent to a wide range of wavelengths in the electromagnetic spectrum.

Figure 3:
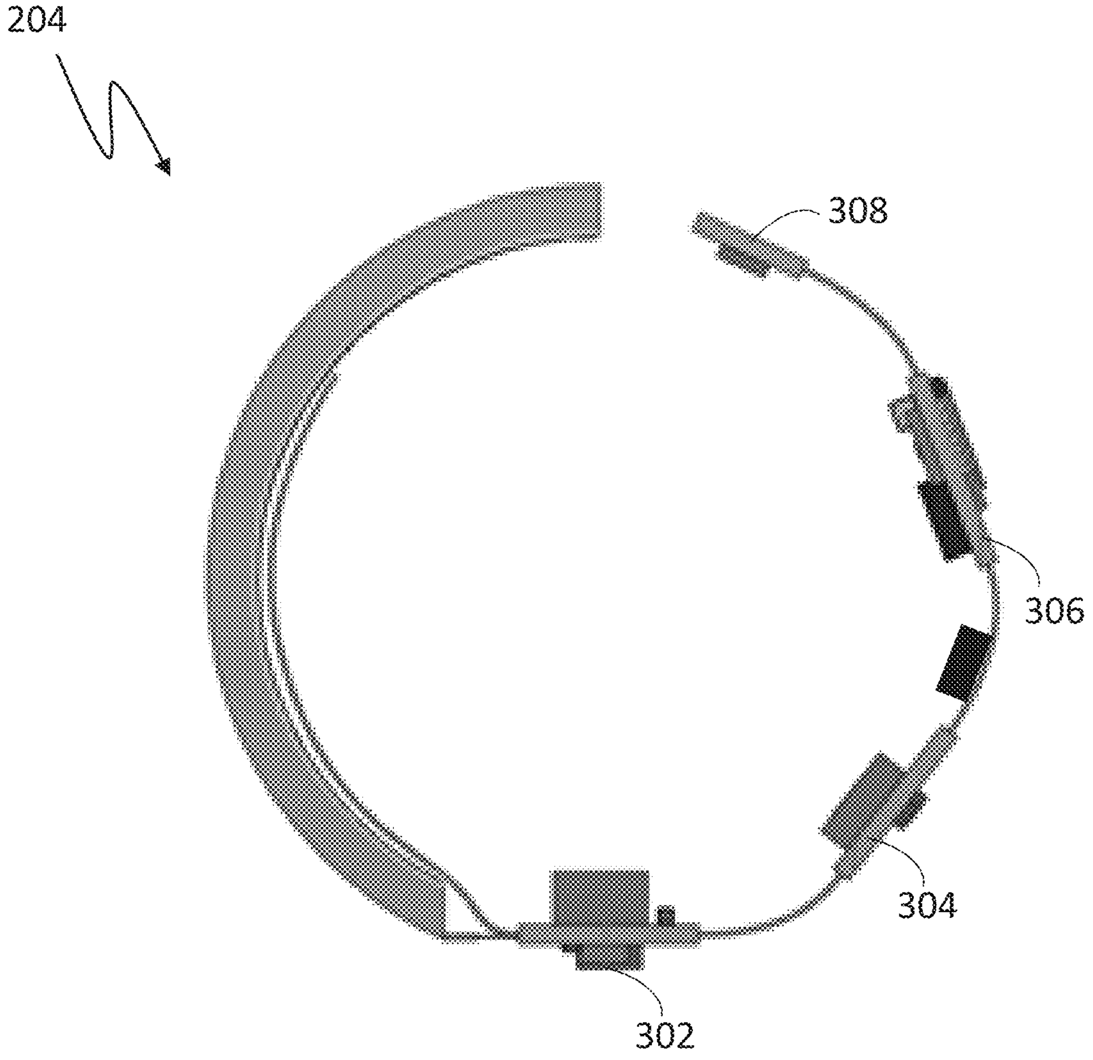
FIG. 3 illustrates a side view of a Printed Circuit Board (PCB) used in the electronic ring, in accordance with an embodiment of the present invention.

FIG. 3 illustrates a side view of the PCB (208), in accordance with an embodiment of the present invention. As illustrated in FIG. 3, the PCB (208) may include a PPG sensor (302). The PPG sensor (302) may calculate blood oxygen saturation (SPO2) level and heart rate of a user. The heart rate of the user may be measured by detecting volumetric variations of blood circulation of the user. The PPG sensor (302) focusses lights of different wavelength lights over the tissue of the user and simultaneously measures the reflected light signals through a photodetector. The transmission and capturing of reflection of the light by the PPG sensor (302) is done through the inner layer (206). The inner layer (206) may be made transparent to allow the PPG sensor (302) to obtain reading from the finger of the user.

The PCB (208) may further include a microcontroller (306). The sensors (302, 304) mounted on the PCB (204) may be connected to the microcontroller (306). The sensors (302, 304) may transmit values of the plurality of health and fitness parameters detected by them to the microcontroller (306), in real-time. The microcontroller (306) may obtain values of the plurality of the health and fitness parameters from the sensors (302, 304) based on some internal and external triggers associated with the sensors (302, 304). The microcontroller (306) may also store values of the plurality of the health and fitness parameters in its own memory or a separate memory element mounted on the PCB (204).

The PCB (208) may be connected with an external user device through a wireless module (308) for communicating with an external user device. The wireless module (308) may work on one or more of Bluetooth and Near Field Communication (NFC). The wireless module (308) may be mounted on the PCB (204) to wirelessly communicate the plurality of health and fitness parameters to the external user device, such as a smartphone or a laptop. The external user device may act as a notification means for the user to access readings of the plurality of health and fitness parameters in a visual or audible format. In another implementation, the PCB (208) may be configured to connect with the external user device through a cloud based platform via a network(s). The battery (210) may be used to power the sensors (302, 304), the micro-controller (306), and the wireless module (308) present in the electronic ring (100).

When a user's hand remains still for a small time period, a difference in intensity of the light focused by the PPG sensor (302) and light reflected from the skin of the user is processed using the one or more machine learning algorithms to predict the skin color of the user. Based on the skin color of the user, the reading of the health and fitness parameter detected by the PPG sensor (302) is optimized.

Figure 4:
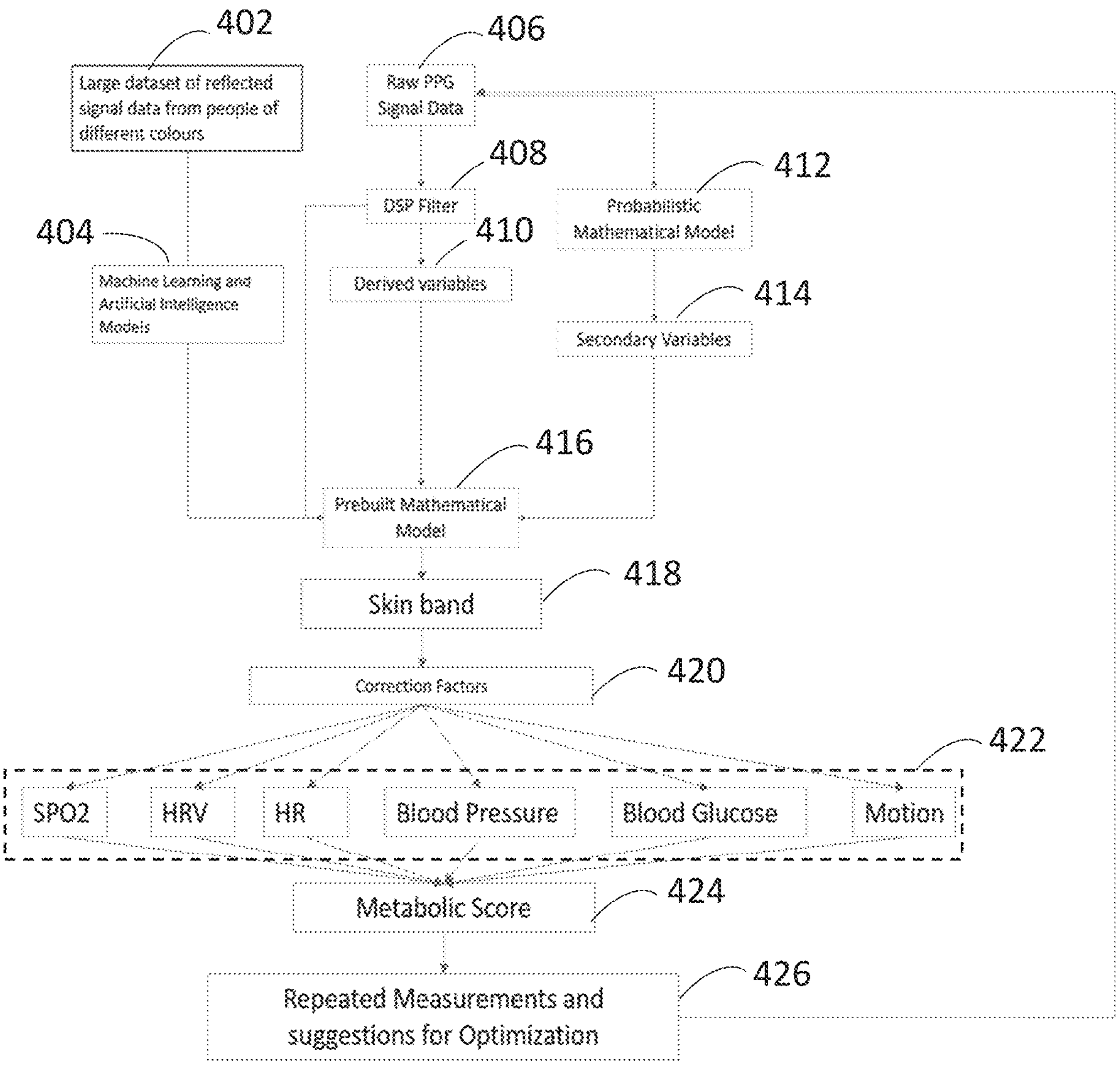
FIG. 4 illustrates computational analysis for optimization of health and fitness parameter readings, in accordance with an embodiment of the present invention.

In another implementation, the PCB (208) may also comprise a color sensor (304) to detect skin color of a user. The color sensor (304) may be an optical sensor that focusses light on to the skin of the user and measures the reflected light signals. The reflected light signals are processed to measure melanin levels in skin of the user, in order to determine the skin color of the user FIG. 4 illustrates computational analysis for optimization of health and fitness parameter readings, in accordance with an embodiment of the present invention. At step 402, a large dataset of reflected light signals captured by the color sensor (304) from the users of different skin colours may be collected. The large dataset may be utilized to train one or more machine learning models, at step 404. One or more machine learning models may include supervised machine learning models such as linear classifiers, Support Vector Machines (SVMs), decision trees, k-nearest neighbor, random forest, and Bayesian classification. The dataset may be used for optimizing readings of the health and fitness parameter measured by the PPG sensor (302).

Raw PPG signal data may be obtained, at step 406. The raw PPG signal data may be filtered using data signal processing, at step 408. Derived variables may be obtained by filtering of the raw PPG signal, at step 410. Further, the raw PPG signal data may be filtered using a probabilistic model, at step 412. Thereafter, secondary variables may be obtained, at step 414. Further, a prebuilt mathematical model may be executed on the optimized reading of the PPG sensor, the derived variables, and the secondary variables, at step 416. A skin color classification band may be obtained, at step 418.

The skin color classification band may be utilized for optimization of health and fitness parameter readings using computational analysis or data modelling. Data models may be trained on skin tones of several people across diverse geographies. The trained data models may be used for optimizing readings of the health and fitness parameter measured by the PPG sensor (302) based on a specific skin tone detected by the color sensor (304). At step 420, values received from the colour sensor (304) may be binned to be classified into multiple categories to determine a skin tone of the user. In an implementation, the values may be classified into six categories based on the "Fitzpatrick skin type scale". The multiple categories may be associated with correction factors. The correction factors may be then multiplied with measured PPG values to obtain corrected values associated with health and fitness parameters of the user, at step 422. The health and fitness parameters of the user may include blood oxygen saturation level (SPO2), heart-rate, Heart Rate Variability (HRV), blood pressure, blood glucose, and motion of the user. The corrected values associated with health and fitness parameters may be utilized to calculate a metabolic score of the user, at step 424, to determine an overall fitness level of the user for people of all skin colors. Repeat measurements of the corrected values associated with health and fitness parameters may be obtained based raw PPG signal data captured in multiple iterations, at step 426. The corrected values associated with health and fitness parameters obtained in each of the multiple iterations may be utilized to improve optimization of the health and fitness parameters of the user.

In one implementation, a combination of the color sensor (304) and the PPG sensor (302) may be used to monitor changes in the skin color of the person wearing the electronic ring (100). The PPG sensor (302) may emit Red and Green coloured lights which are reflected off the user's the skin and measured by the colour sensor (304). The intensity of the reflected light may be classified into six different bands corresponding to the "Fitzpatrick skin type scale" based on empirically determined results. Additional data associated with different bands along with results obtained from the PPG sensor (302) may be used to further confirm the band of the skin color. In case of disputes in the bands identified by the PPG sensor (302) and the colour sensor (304), the values identified by the PPG sensor (302) are further filtered through a probabilistic model to determine the final skin colour band.

The color sensor (304) and the PPG sensor (302) may also detect changes in the way incident light being reflected on the skin to predict a level of body hydration based on skin oil levels and skin moisture levels. The electronic ring (100) continuously studies data obtained from the user to determine the quality of the PPG readings. Confidence on the received PPG readings may be calculated by an auto-correlation function. Value of the auto-correlation function may range from +1 to −1. Variation in the auto-correlation function value may be closely studied to determine variation in the level of body hydration. The values obtained by the PPG sensor (302) in a well hydrated body has good confidence levels and hence has an autocorrelation function value which is closer to +1. A dehydrated body may have lower confidence values and hence has an autocorrelation function value approaching 0. The variations may be then shown as trend-lines. The user of the electronic ring (100) may use the trend-lines as a reference for adjustment of their lifestyle and water intake to improve the level of body hydration. The readings of the PPG sensor (302) on a regular basis may help the user understand more about his body, the way skin color gets affected through absence and over exposure of sunlight, the level of body hydration, and their natural and potentially unnatural skin oil levels. Such parameters may be correlated to other parameters monitored by other wearable devices worn by the user, to provide him a complete analysis of his body and to help him find out the cause of changes occurring in his bodily parameters, over a period of time.

Figure 5A:
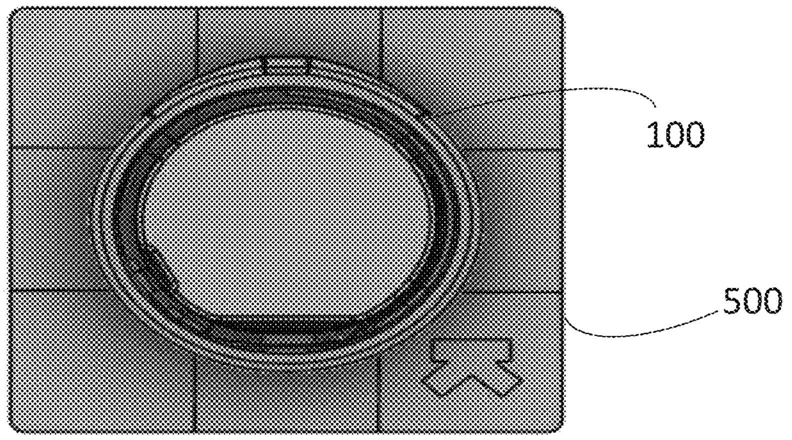
FIGS. 5(*a*) and 5(*b*) illustrate a top view and a side view respectively of the electronic ring placed on a wireless charger, in accordance with an embodiment of the present invention.
Figure 5B:
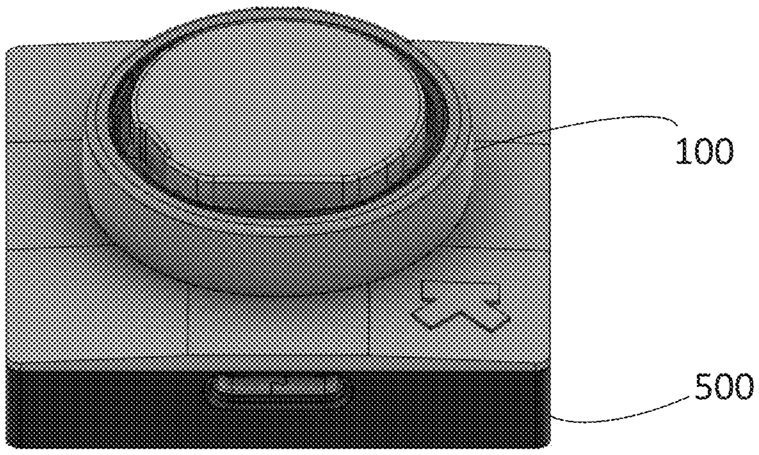

FIGS. 5(*a*) and 5(*b*) illustrate top view and side view respectively of the electronic ring (100) placed on a wireless charger (500), in accordance with an embodiment of the present invention. The electronic ring (100) may be wirelessly chargeable using the wireless charger (500). For wireless charging, the electronic ring (100) may comprise a wireless charging coil. The wireless charging coil may be positioned above or below the PCB (208). Electromagnetic field generated by a coil present in the wireless charger (500) may get coupled with the wireless charging coil of the electronic ring (100) when the electronic ring (100) is present above the wireless charger (500). Through coupling of the electromagnetic field, power may be received and stored in the battery (210). The wireless charger (500) may itself include a battery of capacity sufficient to charge the battery (210) of the electronic ring (100) a few times.

The electronic ring (100) may be worn by a user at all times so that his health and fitness parameters are continuously tracked and reported to him. The electronic ring (100) provides an accurate means for tracking and logging health and fitness parameters of a user in real time. With the data obtained from the electronic ring (100), a user may be able to track changes in his lifestyle, activities, and habits.

In the above detailed description, reference is made to the accompanying drawings that form a part thereof, and illustrate the best mode presently contemplated for carrying out the invention. However, such description should not be considered as any limitation of scope of the present unit. The structure thus conceived in the present description is susceptible of numerous modifications and variations, all the details may furthermore be replaced with elements having technical equivalence

The invention claimed is:

1. A method of determining health and fitness parameters of a user, implemented using a microcontroller, the method comprising:

obtaining, by a colour sensor, intensity values of reflections of light transmitted by the colour sensor on a skin of a user;

classifying, by the microcontroller, the intensity values into a plurality of skin types to determine a skin tone of the user, wherein the plurality of skin types are associated with correction factors;

obtaining, by a Photoplethysmography (PPG) sensor, PPG values associated with health and fitness parameters of the user;

identifying, by the PPG sensor, an estimated skin tone of the user; and multiplying the correction factors and the PPG values to optimize the health and fitness parameters based on the skin tone of the user;

wherein when the estimated skin tone identified by the PPG sensor is different from the skin tone identified by the colour sensor, the method further includes filtering, by a probabilistic model, readings of the PPG sensor to determine a final skin tone.

2. The method as claimed in claim 1, further comprising determining confidence of the readings of the PPG sensor based on a value of an auto-correlation function associated with the readings of the PPG sensor, wherein the value of auto-correlation function ranges from −1 to +1.

3. The method as claimed in claim 2, wherein the value of the auto-correlation function depends on a level of body hydration of the user.

4. The method as claimed in claim 1, wherein the plurality of skin types include six skin types according to Fitzpatrick skin type scale.

5. The method as claimed in claim 1, wherein the health and fitness parameters include one or more of heart-rate, Heart Rate Variability (HRV), a hydration level, and blood oxygen saturation (SPO2) level.

6. An electronic ring for monitoring fitness and health parameters of a user, the electronic ring comprising:

a colour sensor for obtaining intensity values of reflections of light transmitted by the colour sensor on a skin of a user;

a Photoplethysmography (PPG) sensor for obtaining PPG values associated with health and fitness parameters of the user; and a microcontroller configured to:

classifying the intensity values into a plurality of skin types to determine a skin tone of the user, wherein the plurality of skin types are associated with correction factors; and multiplying the correction factors and the PPG values to optimize the health and fitness parameters based on the skin tone of the user;

wherein the PPG sensor further identifies an estimated skin tone of the user, and wherein when the estimated skin tone identified by the PPG sensor is different from the skin tone identified by the colour sensor, readings of the PPG sensor are filtered by a probabilistic model to determine a final skin tone.

* * * * *